United States Patent [19]

Yeboah et al.

[11] Patent Number: 4,497,942
[45] Date of Patent: Feb. 5, 1985

[54] PROCESS FOR HYDROLYZING CHLOROSILANES

[75] Inventors: Yaw D. Yeboah, Schenectady; Michael P. Venditti, Clifton Park, both of N.Y.

[73] Assignee: General Electric Company, Schenectady, N.Y.

[21] Appl. No.: 561,262

[22] Filed: Dec. 14, 1983

[51] Int. Cl.³ .............................................. C08G 77/06
[52] U.S. Cl. ....................................... 528/12; 528/10; 556/459; 556/462
[58] Field of Search .................. 556/462, 459; 528/10, 528/12

[56] References Cited

U.S. PATENT DOCUMENTS 2,758,124  8/1956  Schwenker ........................... 528/10
2,832,794  4/1958  Gordon ................................ 528/10

OTHER PUBLICATIONS

Bulletin 800, Oct. 1981, Chemineer Kenics, Kenics Static Mixers.

Primary Examiner—Melvyn I. Marquis
Attorney, Agent, or Firm—William A. Teoli; James C. Davis, Jr.; James Magee, Jr.

[57] ABSTRACT

A method is provided for hydrolyzing chlorosilanes utilizing a static tubular reactor. A substantial reduction in hydrolysis residence time is achieved.

2 Claims, 1 Drawing Figure

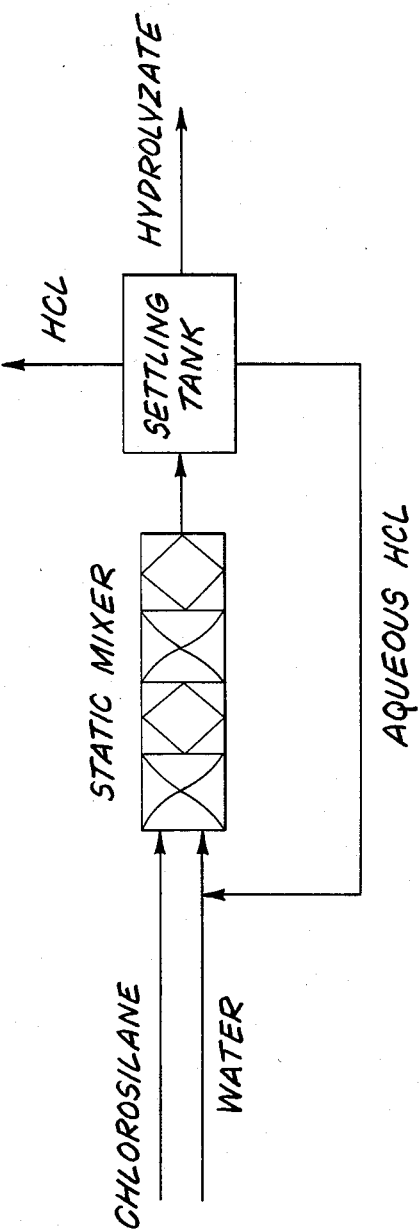

PROCESS FOR HYDROLYZING CHLOROSILANES

BACKGROUND OF THE INVENTION

Prior to the present invention, as shown by Schwenker, U.S. Pat. No. 2,758,124, assigned to the same assignee as the present invention, there was provided a continuous process for the hydrolysis of organohalosilanes in which a two-phase aqueous organohalosilane mixture is pumped continuously through a loop to produce organopolysiloxane hydrolyzate and a 25-36 weight percent hydrochloric acid solution. The pump circulates the reaction mixture in the loop to effect intimate mixing of the reactants and circulation of the resulting organopolysiloxane hydrolyzate and acid. A heat exchanger is also used to achieve good heat transfer. The aqueous hydrochloric acid recovered from the hydrolysis mixture can be distilled to give anhydrous HCl or about a 21% hydrochloric acid solution which can be recycled. Although Schwenker's procedure results in the production of valuable silanol containing polydiorganosiloxane, as well as cyclopolydiorganosiloxane, the hydrolyzate often consists of polydiorganosiloxane having an average of more than 12 chemically combined diorganosiloxy units. The reactivity of such material is often unsuitable for making block copolymers or cyclopolydiorganosiloxane without further modification. In addition, Schwenker's procedure requires a mean residence time of at least 10 minutes for complete conversion of the chlorosilane.

Elaborate efforts have been made by those skilled in the art to minimize molecular weight build-up of organopolysiloxane hydrolyzate generated by chlorosilane hydrolysis. For example, isolation of freshly introduced chlorosilane from the hydrolysis reaction product was the basis of the invention of Gordon, U.S. Pat. No. 2,832,794. Gordon hydrolyzed chlorosilane with either water or aqueous hydrochloric acid which was introduced from a heat exchanger under a pressure of 10-30 psig. The aqueous stream was then passed through an eductor which effected the flow of controlled amounts of liquid chlorosilane. The dual component hydrolysis mixture was then conveyed into a mixing chamber which was followed by a packed column.

The present invention is based on the discovery that low molecular weight silanol terminated polydiorganosiloxane can be made readily by effecting contact in a static tubular reactor, organochlorosilane having the formula,

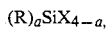

$$(R)_a SiX_{4-a}, \quad (1)$$

and water, or hydrochloric acid, which can be dilute, concentrated or saturated, where R is a C (1-13) monovalent organic radical, X is a halogen radical and a is an integer equal to 1 to 3 inclusive.

Complete conversion of the organochlorosilane of formula (1) to low molecular weight organopolysiloxane hydrolyzate can be achieved in less than about sixty seconds. The present invention also enables a three-phase flow of aqueous HCl, gaseous HCl and organopolysiloxane hydrolyzate in the form of low molecular weight silanol terminated polydiorganosiloxane and cyclopolydiorganosiloxane. The direct evolution of anhydrous HCl as a by-product of the reaction is also provided.

The process of the present invention can be practiced over a wide range of Reynolds Numbers (Re), which defines the degree of turbulence during hydrolysis, where Re is defined as $$Re = (\rho V D / \mu)$$

$\rho$ = density of fluid
$V$ = fluid velocity
$D$ = diameter of static mixer and
$\mu$ = viscosity of the fluid Depending upon the flow rate of the fluid mixture through the static mixer, an Re of less than 10 has been found effective, while a value of greater than 2000 is preferred.

Statement of the Invention

There is provided by the present invention, a process which comprises (1) introducing organochlorosilane and water, or hydrochloric acid in a proportion of from about 10 to 50 moles of water, per mole of organochlorosilane into a static tubular reactor having elements capable of directing material flow radially towards the reactor wall and back to the elements, where the resulting fluid material is conveyed through the reactor at a rate sufficient to achieve a degree of turbulent mixing capable of substantially converting the organochlorosilane to organopolysiloxane within 60 seconds or less, (2) recovering the organopolysiloxane from (1).

Radicals included within R of formula (1) are for example, $C_{(1-8)}$ alkyl radicals, for example, methyl, ethyl, propyl, butyl, pentyl, hexyl, etc.; $C_{(6-13)}$ monovalent aromatic radicals and substituted monovalent $C_{(6-13)}$ aromatic hydrocarbon radicals, for example, phenyl, tolyl, xylyl, chlorophenyl, naphthyl, anthryl, etc.; alkenyl radicals such as vinyl, allyl, etc.

Some of the organochlorosilanes included within formula (1) are, for example, dimethyldichlorosilane, methylchlorosilane, etc.

In order that those skilled in the art will be better able to practice the invention, reference is made to the drawing showing a schematic of a static mixer and a settling tank. Water and organosilane are introduced into the static mixer and products are removed from the settling tank in the form of gaseous and aqueous HCl and organopolysiloxane hydrolyzate.

In the drawing, chlorosilane which is preferably dimethyldichlorosilane and water or aqueous HCl are introduced into the static mixer to effect conversion of the chlorosilane to siloxane hydrolyzate which is sent into a settling tank. Separation of the hydrolyzate from anhydrous HCl and aqueous HCl is thereafter achieved.

Suitable static mixers which can be utilized in the practice of the present invention are, for example, Chemineer-Kenics Static Mixers, Kenics Park, North Andover, Mass. and Koch Static mixers. Depending upon the application, there can be used removable elements available in diameters from ½ inch to 12 inches and fixed elements available in diameters from ½ inch to 24 inches.

It has been found that a flow rate sufficient to maintain a Reynolds number of equal to or greater than 2000 is preferred to achieve a sufficient turbulent flow for better mixing and shorter reaction time for complete chlorosilane conversion. A flow rate of greater than 0.02 feet per second and a total residence time in the reactor of up to about 60 seconds will provide for satisfactory results.

In most instances, the chlorosilane and aqueous feed can be concurrently introduced into the reactor at pressures of from 20 psi to 200 psi to insure an adequate flow rate through the reactor depending upon such factors as the diameter of the static mixer and the viscosity of the fluid reaction mixture.

In particular instances, a heat exchanger can be used to maintain the temperature of the static mixer below about 40° C. during continuous hydrolysis, a jacket can be installed around the static mixer to permit a heat exchange of fluid to circulate in a continuous manner, for example water.

Anhydrous HCl can be collected which can be further reacted with methanol if desired to produce methylchloride. The silicone hydrolyzate in the form of a cyclic siloxane or low molecular weight silanol terminated siloxane, for example, cyclopolydimethylsiloxane or silanol terminated polydimethylsiloxane, can be recovered and used in the manufacture of silicone rubber and silicone block copolymers.

Aqueous HCl can be recovered from the settling tank having a concentration of from about 10% to 42% by weight of hydrogen chloride. The hydrochloric acid can be recycled if desired or it can be further used in the production of intermediates for making organochlorosilanes.

In order that those skilled in the art will be better able to practice the invention, the following examples are given by way of illustration and not by way of limitation. All parts are by weight.

EXAMPLE 1

There was introduced into a stainless steel static mixer having an inside diameter of about ¼ inch, dimethyldichlorosilane and a 40-42% aqueous HCl solution. There was utilized a proportion of about 40-50 moles of water, per mole of dimethylchlorosilane. The average residence time in the mixer was about 5 seconds and the total flow rate of about 0.5 to 0.6 gal of fluid per minute was sufficient to maintain a liquid velocity of greater than 2 feet per second and a Reynolds Number of greater than 2000. A silicone hydrolyzate was obtained having a weight percent of about 6% total chloride consisting of dissolved HCL and chlorine atoms attached to silicon. The silicone hydrolyzate further consisted of 39% by weight of octamethylcyclotetrasiloxane, 49% by weight of total cyclics and about 51% by weight of linear polydimethylsiloxanes and no residual dimethyldichlorosilane. The linear polydimethylsiloxane had an average of about 7.4 dimethylsiloxy units.

The above hydrolysis procedure was repeated except that the dimethyldichlorosilane and a 40-42 weight percent aqueous HCl solution were stirred continuously in a continuous stirred tank reactor maintained at about 19° C. The flow rates of the two streams introduced into the reactor were sufficient to maintain a ratio of greater than 20 moles of water, per mole of dimethyldichlorosilane. The total liquid flow rate resulted in a residence time of about 4 minutes in the reactor. The aqueous phase after it was separated from the hydrolyzate was recycled to the aqueous feed tank. There was obtained a hydrolyzate containing about 5% total chloride in the form of chlorine terminated linear polydimethylsiloxane and dissolved HCL. The hydrolyzate further contained about 41% of octamethylcyclotetrasiloxane, about 53% of total polycylclosiloxane, and no residual dimethyldichlorosilane. The remaining 47% by weight of linear polydimethylsiloxane had an average of about 12.4 dimethylsiloxy units.

Based on the above results those skilled in the art would know that the method of the present invention provides linear polydimethylsiloxane having significantly shorter chain length than methods of the prior art. In addition, it accomplishes complete conversion of the original chlorosilane in a matter of seconds, compared to minutes for the prior art.

EXAMPLE 2

The procedures of Example 1 were repeated except that a hydrolyzate was obtained using the Kenics Static Mixer containing about 7.0% by weight of total chloride, 39% by weight of octamethylcyclotetrasiloxane, 49% by weight of total cyclics, about 51% by weight of linear polydimethylsiloxane and no unreacted dimethyldichlorosilane. The average chain length of the linear polydimethylsiloxane was about 6.3 dimethylsiloxy units.

A hydrolyzate also was obtained employing a similar procedure in the continous stirred tank reactor utilizing dimethyldichlorosilane and the 40-42% by weight of HCL aqueous solution. The hydrolyzate contained about 5.0% by weight of total chloride, 42% by weight of octamethylcyclosiloxane, and 54% by weight of total cyclopolydimethylsiloxane. There was also obtained about 46% by weight of linear polydimethylsiloxane and no unreacted dimethyldichlorosilane. The average chain length of the linear polydimethylsiloxane was about 11 chemically combined dimethylsiloxane units.

Although the above examples are directed to only a few of the very many variables which can be used in the practice of the method of the present invention, it should be understood that the method of the present invention is directed to the use of a much broader variety of static mixers and organochlorosilane than the scope of formula 1.

What we claim as new and desire to secure by Letters Patent of the United States is:

1. A process which comprises,
   (1) introducing organochlorosilane and hydrochloric acid in a proportion of from about 10 to 50 moles of water, per mole of organochlorosilane into a static tubular reactor having elements capable of directing material flow radially towards the reactor wall and back to the elements, where the resulting fluid material is conveyed through the reactor at a rate sufficient to achieve a degree of turbulent mixing capable of substantially converting the organochlorosilane to organopolysiloxane within 60 seconds or less, and where the hydrochloric acid is used at a concentration sufficient to generate anhydrous HCl as a by-product,
   (2) recovering the organopolysiloxane and anhydrous HCl from (1).
2. A method in accordance with claim 1 where the organochlorosilane is dimethyldichlorosilane.

* * * * *